United States Patent [19]
Sanchez

[11] 3,950,432
[45] Apr. 13, 1976

[54] DI- AND TETRA-(PEROXY)KETALS AND ACETALS AND IMPROVED CURING AND POLYMERIZING PROCESS EMPLOYING SAME

[75] Inventor: Jose Sanchez, Grand Island, N.Y.

[73] Assignee: Pennwalt Corporation, Philadelphia, Pa.

[22] Filed: Apr. 10, 1972

[21] Appl. No.: 242,821

[52] U.S. Cl........... 260/610 R; 260/478; 260/526 R; 260/611 A; 260/611 B; 260/75 UA; 260/93.5 S
[51] Int. Cl.².............. C07C 179/00; C07C 179/18
[58] Field of Search........... 260/610 R, 610 A, 488, 260/611 R, 611 A, 611 B, 486, 478 R, 526 R, 586 R, 610 D

[56] References Cited
UNITED STATES PATENTS

| | | | |
|---|---|---|---|
| 2,455,569 | 12/1948 | Dickey | 260/610 B |
| 2,490,282 | 12/1949 | Pezzaglia | 260/610 R |
| 2,537,853 | 1/1951 | Pezzoglia | 260/610 R |
| 2,818,437 | 12/1957 | Wildi | 260/610 R |
| 3,296,184 | 1/1967 | Portulani et al. | 260/41 |
| 3,468,962 | 9/1909 | Ballini et al. | 260/610 R |
| 3,489,730 | 1/1970 | Buttar et al. | 260/80.78 |

FOREIGN PATENTS OR APPLICATIONS

| | | | |
|---|---|---|---|
| 1,293,771 | 4/1969 | Germany | 260/610 R |
| 1,455,684 | 12/1965 | France | 260/610 R |

OTHER PUBLICATIONS

Nazarova et al., *Jour. Organic Chemistry of USSR*, Vol. 2 (2) pp. 249–251 (1966).

*Primary Examiner*—James O. Thomas, Jr.
*Assistant Examiner*—W. B. Lone
*Attorney, Agent, or Firm*—David Edwards

[57] ABSTRACT

Compounds of the general formula

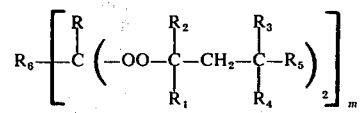

where $m$ is 1 or 2 [e.g., 2,2-di-(t-octylperoxy) propane]; and improved processes using these compounds as initiators for the polymerization of ethylenically unsaturated monomers (such as styrene) and as curing catalysts for curing unsaturated polyester resin compositions.

7 Claims, No Drawings

DI- AND TETRA-(PEROXY)KETALS AND ACETALS AND IMPROVED CURING AND POLYMERIZING PROCESS EMPLOYING SAME

BACKGROUND OF THE INVENTION a. Field of Invention

This invention relates to novel di- and tetra- (t-alkylperoxy) acetals and ketals, and to their use as free-radical initiators in polymerizations of ethylenically unsaturated monomers, as curing catalysts for unsaturated polyester resins and as curing, crosslinking or vulcanizing catalysts for α-olefin polymers and copolymers.

b. Related Art

As a class of peroxides, diperoxyketals (and diperoxyacetals) have been known for more than two decades (U.S. Pat. No. 2,455,569) and, during this time, these peroxides have found use as initiators in vinyl polymerizations, as catalysts for vulcanizing rubbers and as curing agents for polyethylene and ethylene/α-olefin copolymers (see U.S. Pat. Nos. 2,650,913; 2,656,334; 2,692,260; 2,698,311; 3,275,714; 3,296,184; and 3,468,962; Dutch application Ser. Nos. 6,403,775, Jan. 25, 1965, C.A. 62 P 14854 a. and 6,404,319, Apr. 21, 1964, C.A. 64, P 11426 h; Z. F. Nazarova et al., *Zhurnal Organicheskoi Khimii*, vol. 2, No. 2, pp. 259–61, February 1966; and O. M. Mashnenko et al., *Vysokomol. Soedin.*, Ser. B.9 (10), 755–7 (1967) Russ.).

However, most of the diperoxyketals (and diperoxyacetals) reported in the patents and literature and/or commercially available are di(t-butylperoxy) ketals (and acetals) prepared from ketones (and aldehydes) and t-butyl hydroperoxide (as shown in the early 2,455,569 U.S. patent). The above cited Mashnenko et al. article did some studies with t-amyl and t-hexyl hydroperoxides and found that the rates of polymerization of styrene using the di(t-amyl and t-hexylperoxy)-hexane derivatives were similar to that of di(t-butylperoxy) hexane (1.09: 1.20: 1, respectively).

U.S. Pat. No. 3,488,392 and German OLS No. 1,923,085 describe various substituted diperoxyketals.

BRIEF SUMMARY OF THE INVENTION

This invention concerns:

A. Compounds of the formula:

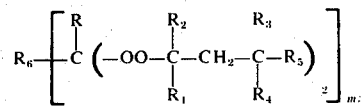

where
1. $m$ is 1 or 2 (preferably 1);
2. $R_1$, $R_2$, $R_3$ and $R_4$ are alkyl of 1–4 carbons (preferably methyl);
3. $R_5$ is alkyl of 1–8 carbons (preferably methyl); and
4. R and $R_6$ are the same or different and, when $m$ is 1, are substituted or unsubstituted alkyl of 1–10 carbons, alkenyl of 2–10 carbons, alkdienyl of 3–10 carbons, cycloalkyl of 3–10 carbons, cycloalkenyl of 3–10 carbons, aralkyl of 7–10 carbons or hydrogen, $R_6$ can also be aryl of 6–14 carbons (preferably phenyl) or 4–6 membered heterocyclic when R is H, and R and $R_6$ can join together to form a substituted or unsubstituted alkenylene or alkylene diradical of 3–11 carbons; and, when $m$ is 2, the two Rs can have the same definition as above and can additionally join to form a substituted or unsubstituted alkylene diradical having 1–3 carbons in the alkylene chain and $R_6$ is a substituted or unsubstituted alkylene diradical having 1–8 carbons in the alkylene chain or, if both Rs are hydrogen, a substituted or unsubstituted phenylene diradical;

the substituents being one or more of (the alkyl portions having 1–4 carbons) alkyl, halo, cyano, isocyanato, azido, amino, carboxy, alkoxycarbonyl, aroyl, alkoxy, aryloxy, aminocarbonyl and nitro; and B. Improved processes for
1. polymerizing ethylenically unsaturated monomers which are responsive at suitable temperatures to initiating amounts of free radical polymerization initiators; and
2. curing unsaturated polyester resin compositions by heating in the presence of initiating amounts of free radical curing catalysts, the improvement residing in the use of a compound described in (A) as said initiator or curing catalyst.

DETAILED DESCRIPTION OF INVENTION

It has now been discovered that the above di-(and tetra)peroxyketals (and acetals) can be prepared by acid condensations of aldehydes and ketones with $C_8$ and higher t-alkyl hydroperoxides (t =tertiary), preferably 1,1,3,3-tetramethylbutyl (hereinafter referred to as t-octyl) hydroperoxide, and that these peroxides give faster cures of unsaturated polyester resins and greater polymerization rates and weight and equivalent efficiencies in the polymerization of ethylenically unsaturated monomers than the heretofore used di-(t-butylperoxy) ketals derived by condensation of the same ketone.

COMPOUNDS

The above-described di(or tetra)-(t-$C_8$-$C_{23}$ alkylperoxy) ketals and acetals of this invention can be prepared by acid condensation of ketones, aldehydes, diketones and dialkdehydes with appropriate t-alkyl hydroperoxides by methods well-known in the art.

The following table list examples of t-alkyl hydroperoxides, aldehydes and ketones operable in these processes:

TABLE I t-Alkyl Hydroperoxides 1,1,3,3-tetramethylbutyl (or t-octyl) hydroperoxide
1,1,3,3,5,5-hexamethylhexyl (or t-dodecyl)hydroperoxide
Other 3,3,3-trialkylsubstitutedtertiaryalkyl hydroperoxides such as:

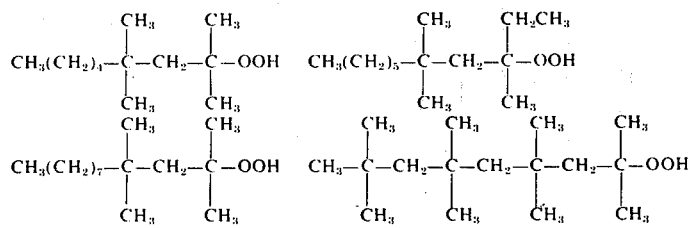

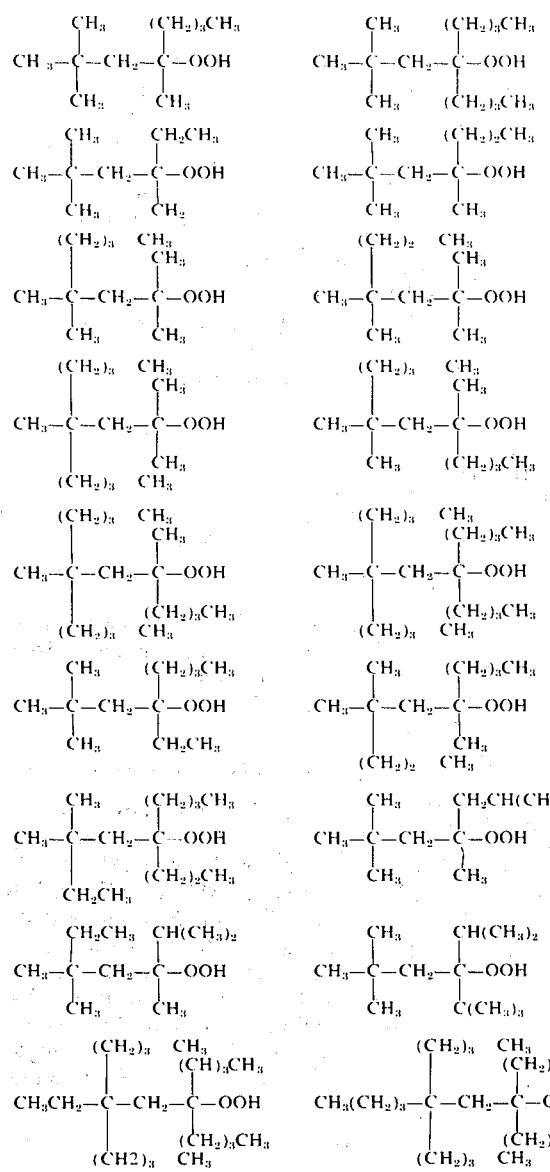

Hydroperoxides such as those listed above can be prepared by the various methods outlined in "Organic Peroxides", Vol. I, Edited by D. Swern, John Wiley & Sons, Inc., N.Y., 1970, Chapter I, "Organic Peroxides and Peroxy Compounds — General Description", by O. L. Mageli and C. S. Sheppard, pp. 4–17.

Briefly, the procedures are: (a) Addition of hydrogen peroxide to the corresponding olefin in the presence of Lewis acids; (b) Reaction of hydrogen peroxide with the corresponding tertiary alcohol in the presence of Lewis acids; (c) Reaction of hydrogen peroxide with the corresponding t-alkyl halide, alkylsulfonate, sulfate, etc., under neutral or basic conditions; and (d) Autoxidation of the corresponding hydrocarbon.

TABLE II

| Class | Aldehydes and Dialdehydes Examples |
|---|---|
| Alkyl-saturated | acetaldehyde, butyraldehyde, isobutyraldehyde, 2-ethylbutyraldehyde, lauraldehyde, formaldehyde propionaldehyde, pivaldehyde |
| Alkyl-unsaturated | acrolein, citral |
| Cycloalkyl | cyclohexanecarboxaldehyde, cyclopentanecarboxaldehyde |
| Substituted alkyl | 4-chlorobutyraldehyde, 3-chloropropionaldehyde |
| Aryl | benzaldehyde, furfural, p-tolualdehyde |
| Substituted aryl | p-chlorobenzaldehyde |
| Aralkyl | 3-phenylpropionaldehyde |
| Dialdehyde | terephthalaldehyde, malonaldehyde, isophthalaldehyde, phthalaldehyde |

TABLE III

| Class | Ketones and Diketones Examples |
|---|---|
| Alkanones | acetone, 2-butanone, 4-methyl-2-pentanone, 2-pentanone, 3-pentanone, 3-heptanone, 5-methyl-3-heptanone, 4-heptanone, 2,6-dimethyl-4-heptanone, 2-hexanone, 4,4-dimethyl-2-pentanone, 3-methyl-2-butanone, 5-methyl-2-hexanone, 3,3-dimethyl-2-butanone, 2,4-dimethyl-3-pentanone, methyl cyclopentyl ketone, methyl cyclohexyl ketone, |

| Class | Ketones and Diketones Examples |
|---|---|
| Alkenones | methyl 2-cyclohexenyl ketone, methyl cyclopropyl ketone methyl vinyl ketone, mesityl oxide, 2-methyl-2-hepten-6-one |
| Substituted alkanones | 1-chloroacetone, 1-cyanoacetone, ethyl acetoacetate, levulinic acid, 1-phenylacetone, 1-aminoacetone, 1-azidoacetone, 1-nitroacetone, 3-oxobutyl isocyanate, acetoacetamide, n-butyl levulinate, ethyl 12-oxostearate, benzoylacetone, 2-ethoxycarbonylcyclopentanone, 4-phenyl-2-butanone, 1,3-diphenylacetone |
| Cycloalkanones | cyclopentanone, cyclohexanone, cyclododecanone, 2-methylcyclohexanone, 4-t-butylcyclohexanone, 3,3,5-trimethylcyclohexanone, cyclobutanone, 2,2,4-trimethylcyclopentanone, 3-methylcyclohexanone, cycloheptanone |
| Substituted cycloalkanones | 2-chlorocyclohexanone |
| Cyclohexenones | 2-cyclohexen-1-one, isophorone |
| Alkanediones and Cycloalkanediones | 2,4-pentanedione, 3-methyl-2,4-pentanedione, 2,5-hexanedione, 1,3-cyclohexanedione, 1,4-cyclohexanedione, 2,11-dodecanedione |

The following are representative examples of compounds of this invention:
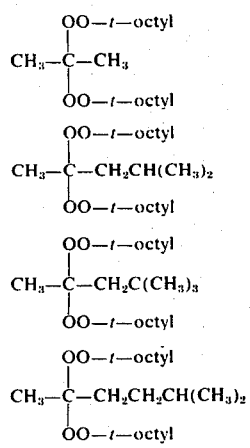
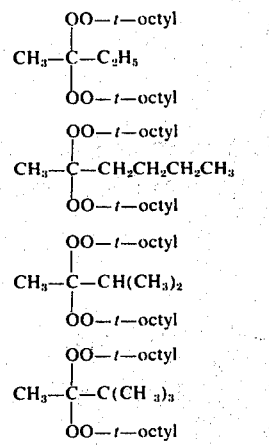
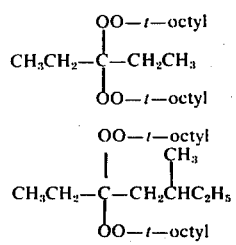
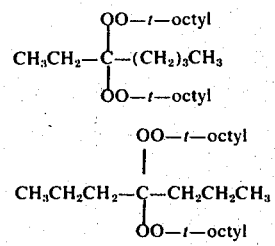
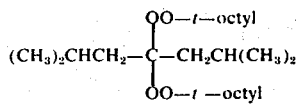
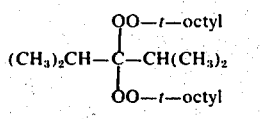
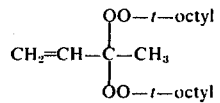
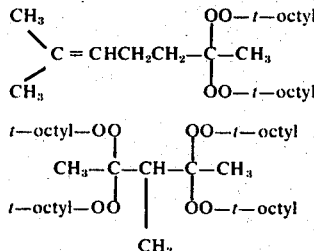
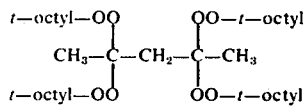
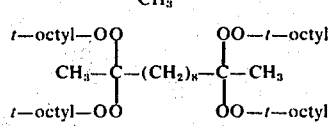
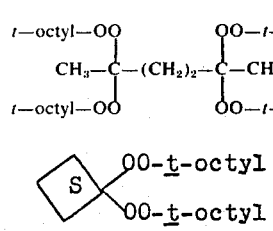
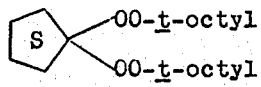
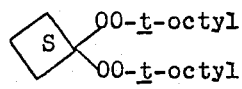
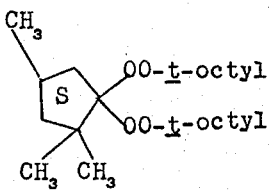
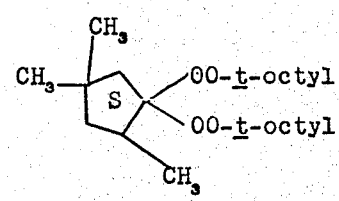
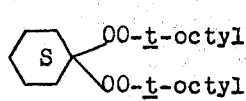
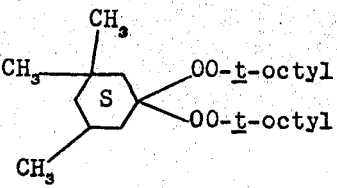

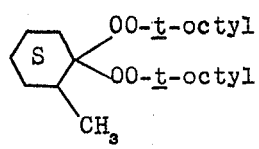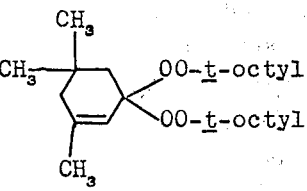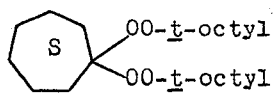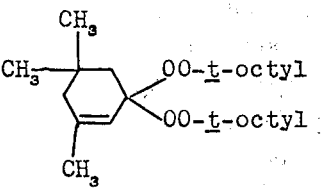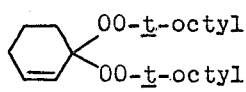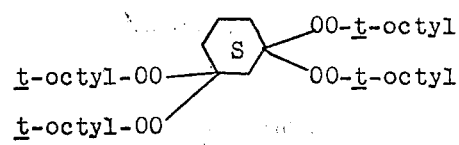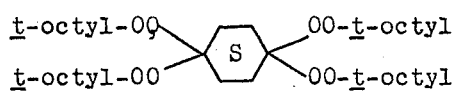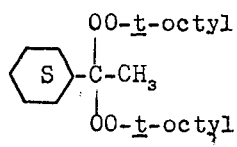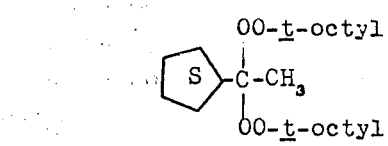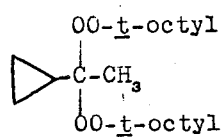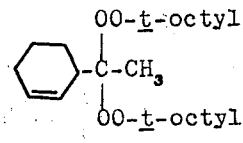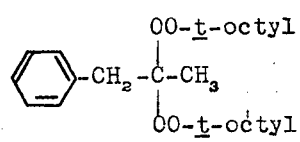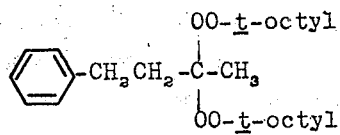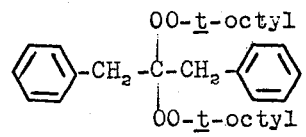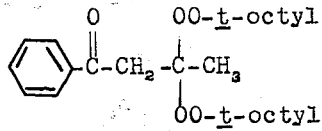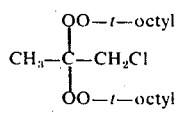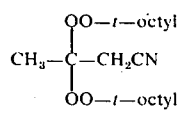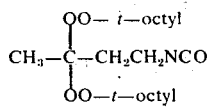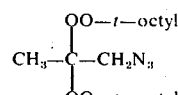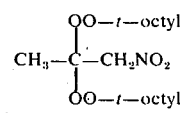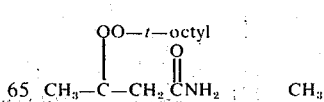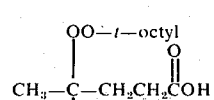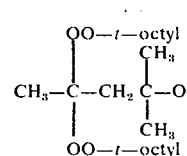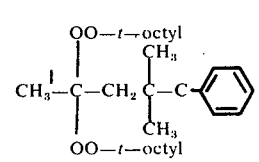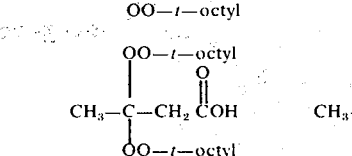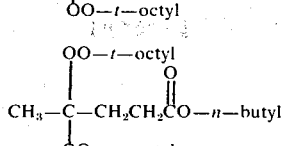

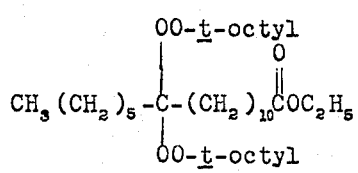
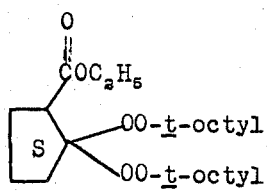
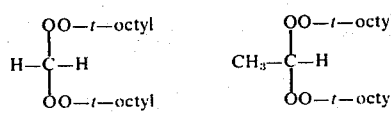
10
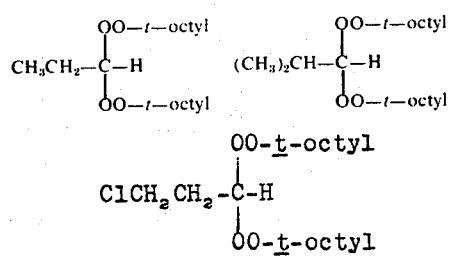
15
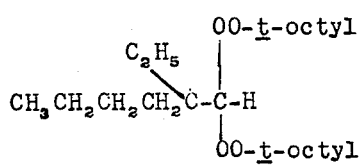
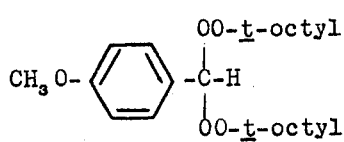
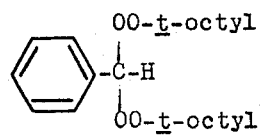
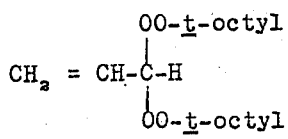
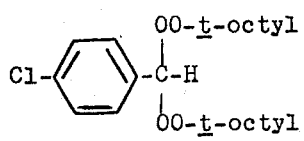
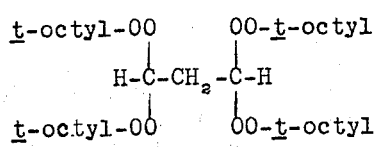
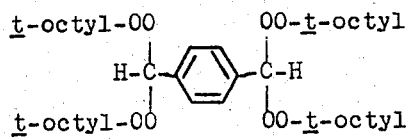
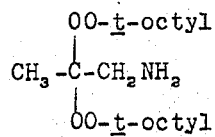
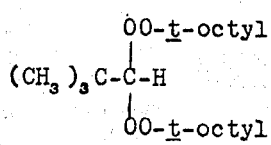
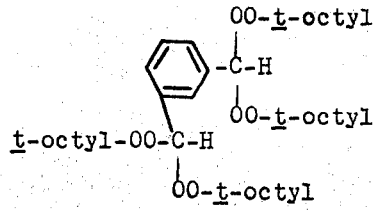
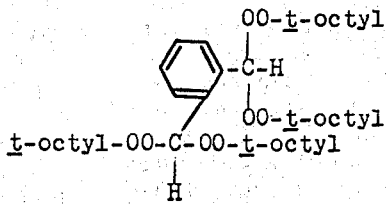

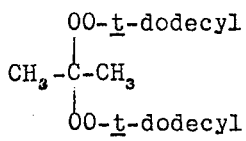 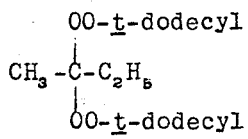

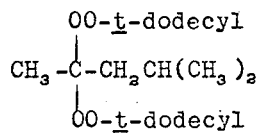 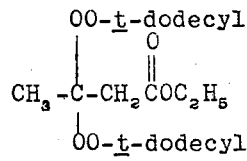

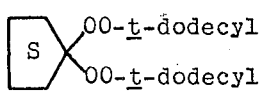 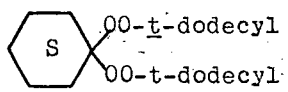

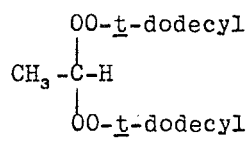 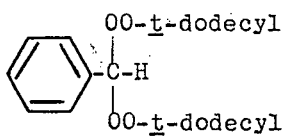

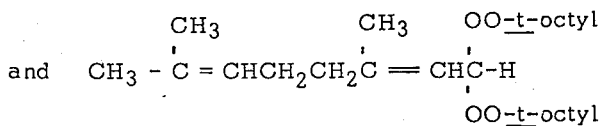

While only derivatives of t-octyl and t-dodecyl hydroperoxides are shown above in the interest of saving space, it should be understood that $R_1$, $R_2$, $R_3$ and $R_4$ in the above compounds can also be lower alkyl of 2–4 carbons and that $R_5$ can also be alkyl of 2–8 carbons.

Preferred compounds include those shown in Table IV below, especially 2,2-di-(t-octylperoxy) propane; 2,2-di-(t-octylperoxy) butane; 4-methyl-2,2-di-(t-octylperoxy) pentane; and 2,2-di-(t-octylperoxy)-hexane.

POLYMERIZATION

In the free-radical initiated polymerization of ethylenically unsaturated monomers at suitable temperatures, the subject peroxides are found to provide high polymerization rates and high weight and equivalent efficiencies, especially in comparison to art-related di-(t-butylperoxy)ketals and t-butyl peroxybenzoate (a well-known industrial polymerization initiator).

Suitable monomers include olefins such as ethylene, propylene, styrene (a preferred monomer), vinyltoluene, vinylpyridine, divinylbenzene, and α-methylstyrene; conjugated olefins such as 1,3-butadiene, isoprene and chloroprene; vinyl esters such as vinyl acetate, vinyl propionate, vinyl laurate, vinyl benzoate and divinyl carbonate; allyl esters such as allyl acetate, diallyl carbonate, allyl benzoate and diallyl phthalate; unsaturated conjugated nitriles such as acrylonitrile and methacrylonitrile; acrylic acid and methacrylic acid and their esters and amides such as methyl, ethyl, n-butyl and 2-ethylhexyl acrylates and methacrylates and acrylamide and methacrylamide; maleic anhydride; maleic acid and fumaric acid and their esters; vinyl halo and vinylidene halo componds such as vinyl, chloride, vinyl bromide, vinyl fluoride, vinylidene chloride and vinylidene fluoride; perhalo olefins such as tetrafluoroethylene, hexafluoropropylene and chlorotrifluoroethylene; vinyl ethers such as methyl vinyl ether and n-butyl vinyl ether; acrolein; and mixtures thereof.

Temperatures of about 20°–300°C. (preferably 50°–250°C.) and peroxide levels of about 0.005–5.0% or more (preferably 0.05–5.0%) by weight, based on the monomer, are normally employed in these processes. Conventional solvents may optionally be added to the reaction system.

CURING OF POLYESTER RESINS

In curing unsaturated polyester resin compositions by heating at suitable curing temperatures in the presense of free radical curing catalysts, the use of the peroxides of this invention are found to result in faster cures (have unexpectedly higher activity) than the conventional di-(t-butylperoxy) ketals.

Unsaturated polyester resins curable by the subject peroxides normally consist of an unsaturated polyester and a polymerizable monomer. The unsaturated polyester component is normally obtained by the esterification of one or more, preferably ethylenically unsaturated,, di-or polycarboxylic acid or their anhydrides, such as maleic acid, fumaric acid, glutaconic acid, itaconic acid, mesaconic acid, citraconic acid, allyl malonic acid, allyl succinic acid, and others, with saturated or unsaturated polyalcohols such as ethylene glycol; diethylene glycol (2,2'-dihydroxy ethyl ether); triethylene glycol (ethylene glycol bis-(2-hydroxy ethyl ether); propanediol-1,2; butanediol-1,3; 2,2-dimethyl propanediol-1,3; butene (2)-diol-1,4; glycerol, pentaerythritol, mannitol, and others. Mixtures of such acids and/or alcohols may also be used. The unsaturated di- or polycarboxylic acids may be replaced, at least partly, by saturated carboxylic acids such as adipic acid, succinic acid, sebacic acid, and others, or by aromatic dicarboxylic acids, such as phthalic acid, tetrahydrophthalic acid, and others and their anhydrides such as phthalic anhydride. The acids used as well as the alcohols employed may be substituted by other substituents, preferably by halogen. Examples of suitable halogenated acids are, for instance, tetrachloro phthalic acid; 1,4,5,6,7,7-hexachloro bicyclo (2,2,1) heptene (5)-2,3-dicarboxylic acid, and others, or their anhydrides.

The other component of the unsaturated polyester resin compositions are unsaturated monomers, preferably ethylenically unsaturated monomers such as styrene, vinyl toluene, methyl methacrylate, diallyl phthalate, dibutyl fumarate, acrylonitrile, triallyl cyanurate, α-methyl styrene, divinyl benzene, methyl acrylate, diallyl maleate, n-butyl methacrylate, ethyl acrylate, and others, which are copolymerizable with said polyesters.

A preferred resin composition contains as the polyester component the esterification product of propylene glycol (a polyalcohol), maleic anhydride (anhydride of an unsaturated dicarboxylic acid) and phthalic anhydride (anhydride of an aromatic dicarboxylic acid) and as the monomer component styrene.

Temperatures of about 20°–250°C. (preferably 50–200°C.) and peroxide levels of about 0.05–5.0% or more (preferably 0.2–2.5%) by weight of curable unsaturated polyester resin are normally employed.

OTHER USES

Furthermore, the peroxides of this invention can be used in other applications such as in vulcanizing of natural and synthetic rubbers, and for vulcanizing, curing or crosslinking of olefin polymers such as polyethylene, olefin copolymers such as ethylene-propylene copolymers and olefin terpolymers such as ethylene-propylene-diene terpolymers, in the presence and absence of additives and fillers such as sulfur, carbon black, silica, blowing agents, stabilizers, ultraviolet absorbers, etc. In such applications 0.1% to 5% or more by weight of vulcanizable, curable or crosslinkable polymer, copolymer or terpolymer can be employed.

EXAMPLES

The following examples illustrate the subject invention but are not in limitation thereof.

EXAMPLE I — Preparation of 2,2-Di-(t-Octylperoxy) Propane

To a jacketed reactor was charged 7.0g. (0.12 mole) of acetone, 39.2g. (0.24 mole) of 1,1,3,3-tetramethylbutyl hydroperoxide (89.7% assay) and 120 ml. of pentane. To the vigorously stirred solution at 0°C was added 16g. of 77% sulfuric acid over a period of 30 minutes and the reaction mixture was allowed to stir at 0°C for 4 hours. The pentane layer was then separated, washed with water, then aqueous 10% KOH solution and finally with water to neutral and was dried over anhyd. MgSO$_4$. After separation of the desiccant and vacuum stripping, 21.3g. (53.1% of theory, uncorr.) of liquid remained which had an "active oxygen" content of 8.66% (theory, 9.64%). Hence, the assay was 90% and the corrected yield was 47.8%. An infrared spectrum of the product showed no O—H or C=O bands but showed a strong OO band at 860 cm$^{-1}$.

EXAMPLE II — Preparation of 2,2-Di-(t-Octylperoxy)Butane

To a jacketed reactor was charged 8.36g. (0.116 mole) of 2-butanone, 38.0g. (0.232 mole) of 1,1,3,3-tetramethylbutyl hydroperoxide (89.7% assay) and 100 ml. of pentane. To the vigorously stirred mixture at 0°C was added 17.2g. of 77% sulfuric acid over a period of 15 minutes and the mixture was allowed to stir at 0°C for 4 hours. The product was worked up as in Example I and 23.8g. (59.5% of theory, uncorr.) of liquid was obtained which had an active oxygen content of 8.41% (theory, 9.25%). Hence, the assay of the product was 91.0% and the corrected yield was 54.2%. An infrared spectrum of the product showed no OH or C=O bands but showed a strong and broad OO band centered at 875 cm$^{-1}$.

EXAMPLE III— Preparation of Other Gem-Di-(t-Octylperoxy)Alkanes

Following essentially the same procedure employed in Examples I and II, several other gem-di-(t-octylperoxy)alkanes were prepared from various ketones and aldehydes. The yields and assays of the peroxides produced are summarized in Table IV. The yields and assays of the peroxides produced from the reactions described in Examples I and II are also included for comparison purposes. These results show that usually reaction temperatures below 0°C give products in better assays and yields than do reaction temperatures of 0°C of higher.

Table IV

| | Gem-Di-(t-Octylperoxy)Alkanes | | | | |
|---|---|---|---|---|---|
| | | % Corr. Yield | | Assay, % | |
| Ketone or Aldehyde | Peroxide Produced | 0°C | −20 to −15°C | 0°C | −20 to −15°C |
| Acetone | 2,2-di-(t-octylperoxy)propane | 47.8 | — | 90.0 | — |
| 2-Butanone | 2,2-di-(t-octylperoxy)butane | 54.2 | — | 91.0 | — |
| 3-Pentanone | 3,3-di-(t-octylperoxy)pentane | 17.3 | 69.2 | 55.8 | 70.8 |
| 3-Methyl-2-butanone | 3-Methyl-2,2-di-(t-octylperoxy)butane | 53.2 | — | 92.1 | — |
| 2-Hexanone | 2,2-di-(t-octylperoxy)hexane | 75.5 | 98.0 | 96.3 | 100 |
| 4-Methyl-2-pentanone | 4-Methyl-2,2-di-(t-octylperoxy)pentane | 40.7 | 76.4 | 86.4 | 90.3 |
| 3-Heptanone | 3,3-di-(t-octylperoxy)heptane | — | 91.0 | — | 97.2 |
| 4-Heptanone | 4,4-di-(t-octylperoxy)heptane | 87.1 | — | 93.2 | — |
| 2-Methyl-2-hepten-6-one | 2-Methyl-6,6-di-(t-octylperoxy)-2-heptene | 90.2 | — | 92.0 | — |
| Ethyl Acetoacetate | ethyl 3,3-di-(t-octylperoxy)butyrate | 77.5 | 79.0 | 100 | 96.9 |
| n-Butyl Levulinate | n-butyl 4,4-di-(t-octylperoxy)valerate | 95.4 | 79.4 | 97.1 | 88.7 |
| Levulinic Acid | 4,4-di-(t-octylperoxy)valeric acid | — | 15.5 | — | 61.9 |
| Cyclohexanone | 1,1-di-(t-octylperoxy)cyclohexane | 52.0 | 61.7 | 77.5 | 78.5 |
| 2-Methylcyclohexanone | 2-Methyl-1,1-di-(t-octylperoxy)cyclohexane | 35.6 | 80.4 | 69.8 | 82.3 |
| 3-Methylcyclohexanone | 3-Methyl-1,1-di-(t-octylperoxy)cyclohexane | — | 85.2 | — | 87.7 |
| 3,3,5-Trimethylcyclohexanone | 3,3,5-trimethyl-1,1-di-(t-octylperoxy)cyclohexane | 57.5 | 84.5 | 67.6 | 89.0 |
| 2,4 Pentanedione | 2,2,4,4-tetra-(t-octylperoxy)pentane | 40.0 | — | 86.4 | — |
| Benzaldehyde | 1,1-di-(t-octylperoxy)-1-phenylmethane | 42.3 | 81.0 | 65.4 | 90.4 |
| Furfuraldehyde | 1-(2'-furyl)-1,1-di-(t-octylperoxy)-methane | 55.0 | — | 81.0 | — |
| Citral | 3,7-dimethyl-1,1-di-(t-octylperoxy)-2,6-octadiene | — | 65.8 | — | 87.8 |

EXAMPLE IV — 100°C(212°F)SPI Exotherms of Di-(t-Octylperoxy)ketals

The unsaturated polyester resin employed in this example was a mixture of an unsaturated polyester and styrene monomer.

The unsaturated polyester was an alkyd resin made by esterifying the following components:

| Component | Quantity |
| --- | --- |
| Maleic anhydride | 1.0 mole |
| Phthalic anhydride | 1.0 mole |
| Propylene glycol | 2.2 moles |

To the resulting resin was added 0.013% by weight of hydroquinone inhibitor. The alkyd resin had an Acid No. of 45–50. Seven parts by weight of the above polyester (alkyd resin) was diluted with three parts by weight of monomeric styrene. The resulting unsaturated polyester resin had the following properties:

| | |
| --- | --- |
| a. Viscosity (Brookfield No. 2 at 20 r.p.m.) | 13.08 poise |
| b. Specific gravity | 1.14 |

CURING PROCEDURE

Gelation and cure characteristics of various initiators in the unsaturated polyester resin described above were determined using the Standard SPI Exotherm procedure ("SPI Procedure for Running Exotherm curves — Polyester Resins", published in the Preprint of the 16th Annual Conference — Reinforced Plastics Division, Society of the Plastics Industry, Inc., February, 1961).

Using this procedure, the diperoxyketals of this invention were evaluated as curing catalysts for the unsaturated polyester resin at 100°C. The catalyst concentration was at an active oxygen level equal to 0.8% by weight of resin of t-butyl peroxybenzoate (a well-known industry standard for polyester curing). The resulting data are summarized in the table below:

| No. | Peroxide | Gel, Min. | Cure, Min. | Peak Exo., °F | Barcol Hardness |
| --- | --- | --- | --- | --- | --- |
| (1) | 2,2-di-(t-octylperoxy)-Propane | 5.1 | 6.8 | 420 | 35–40 |
| (2) | 2,2-di-(t-butylperoxy)-propane | 6.4 | 8.6 | 416 | 40 |
| (3) | 2,2-di-(t-amylperoxy)-propane | 4.7 | 7.8 | 418 | 30–35 |
| (4) | 2,2-di-(α-cumylperoxy)-propane | 8.8 | 11.4 | 415 | 40 |
| (5) | 2,2-di-(t-octylperoxy)-butane | 3.9 | 5.3 | 427 | 35–45 |
| (6) | 2,2-di-(t-butylperoxy)-butane | 4.7 | 6.5 | 416 | 40 |
| (7) | t-butyl peroxybenzoate | 11.8 | 14.3 | 414 | 35–40 |

These data show that the di-(t-octylperoxy)ketals of this invention (Nos. (1) and (5)) have significantly higher activities in the unsaturated polyester resin at 100°C than equal molar levels of di-(t-butylperoxy)ketals, di-(t-amylperoxy)ketals and di-(α-cumylperoxy)ketals (art peroxides prepared from the same ketone).

EXAMPLE V — 100°C 10% Styrene Polymerization Rates

At 0°C $5.0 \times 10^{-4}$ equivalents of various diperoxyketals were added to exactly 100 ml. portions of styrene. Rates of styrene polymerization at 100°C were determined dilatometrically and the rates at 10% conversion are shown in Table V and are compared to that of t-butyl peroxybenzoate (an industrial standard). The 10% conversion rates at 100°C for styrene polymerizations initiated by the di-(t-octylperoxy)ketals of this invention (Nos. (4), (6), (8) and (10)) are considerably greater than the 10% styrene polymerization rates caused by di-(t-butylperoxy)-ketals, di-(t-amylperoxy)-ketals and di-(α-cumylperoxy)ketals from the same ketones and t-butylperoxybenzoate. The 10% conversion rates caused by the di-(t-octylperoxy)ketals are about 100% greater than those caused by the di-(t-butylperoxy)-ketals of the same ketones.

Table V

| No. | Peroxide | 10% Conversion Styrene Polymerization Rates at 100°C | |
| --- | --- | --- | --- |
| | | Rate[1] | Relative Rate[2] |
| (1) | 2,2-di-(t-butylperoxy)-propane | 6.47 | 0.67 |
| (2) | 2,2-di-(t-amylperoxy)-propane | 7.91 | 0.83 |
| (3) | 2,2-di-(α-cumylperoxy)-propane | 8.94 | 0.94 |
| (4) | 2,2-di-(t-octylperoxy)-propane | 13.48 | 1.42 |
| (5) | 2,2-di-(t-butylperoxy)-butane | 9.02 | 0.95 |
| (6) | 2,2-di-(t-octylperoxy)-butane | 16.30 | 1.72 |
| (7) | 2,2-di-(t-butylperoxy)-4-methylpentane | 11.48 | 1.26 |
| (8) | 4-methyl-2,2-di-(t-octylperoxy)pentane | 20.57 | 2.17 |
| (9) | 2,2-di-(t-butylperoxy)-hexane | 9.46 | 1.00 |
| (10) | 2,2-di-(t-octylperoxy)-hexane | 17.21 | 1.81 |
| (11) | t-butyl peroxybenzoate | 9.49 | 1.00 |

[1] $\times 10^3$ moles of styrene/liter/min.
[2] t-butyl peroxybenzoate = 1.00

EXAMPLE VI — High Conversion Styrene Polymerization Efficiencies of Various Diperoxyketals at 100°C/8.5 Hours For each initiator evaluated, a series of Pyrex glass tubes was filled with styrene solutions containing varying amounts of free-radical initiator and sealed, several tubes being used for each initiator. Amounts of the free-radical initiators in the tubes were adjusted so that the resulting % conversion versus concentration plots would cross about 97% conversion after 8.5 hours at 100°C. After 8.5 hours at 100°C, the tubes were removed from a thermostated bath and quickly chilled to −20°C to prevent any post-polymerization. The sealed tubes were then broken and the contents were dissolved in benzene. Each benzene solution was then poured into a large excess of methanol and the resulting polymer was separated by filtration and dried in an oven at 50°–55°C. The % conversion of styrene to polymer was then determined and plots of initiator level versus % conversion were constructed. The initiator levels required to attain about 97% conversion at 100°C for 8.5 hours relative to those of t-butylperoxybenzoate (an industry standard initiator for styrene polymerizations) under the same conditions were determined. The weight and equivalent efficiencies (E and W, respectively) of the invention diperoxyketals and art diperoxyketals, relative to those of t-butylperoxybenzoate, are summarized in Table VI. The lower the values of W and E, the greater the efficiencies on weight and equivalent bases, respectively. These data show that the di-(t-octylperoxy)ketals of this invention (Nos. (1), (3) and (5)) are not only much more efficient than t-butylperoxybenzoate, but also very significantly more efficient than the art diperoxyketals (Nos. (2), (4) and (6)).

The unusual and unexpected feature about the high conversion efficiencies of the diperoxyketals of this invention (Nos. (1), (3) and (5)) is that they have significantly better weight efficiencies in styrene polymerizations at 100°C than have comparable di-(t-butylperoxy)ketals such as Nos. (2), (4) and (6) even though the molecular weights of Nos. (1), (3) and (5) are very much higher.

Hence, Examples V and VI show that the di-(t-octylperoxy)-ketals of this invention are significantly more efficient in high conversion styrene polymerizations and bring about much higher rates of polymerization of styrene than the art diperoxyketals and t-butyl peroxybenzoate.

Table VI

100°C/8.5 Hours - High Conversion Styrene Polymerization Efficiencies of Diperoxyketals Relative to t-Butyl Peroxybenzoate

| No. | Peroxide | % Conversion | W | E |
|---|---|---|---|---|
| (1) | 2,2-di-(t-octylperoxy)-propane | 97.0 | 0.56 | 0.65 |
| (2) | 2,2-di-(t-butylperoxy)-propane | 97.0 | 1.21 | 2.13 |
| (3) | 2,2-di-(t-octylperoxy)-butane | 98.5 | 0.41 | 0.46 |
| (4) | 2,2-di-(t-butylperoxy)-butane | 98.5 | 0.59 | 0.98 |
| (5) | 4-methyl-2,2-di-(t-octylperoxy)pentane | 98.5 | 0.35 | 0.37 |
| (6) | 2,2-di-(t-butylperoxy)-4-methylpentane | 98.5 | 0.56 | 0.83 |

What is claimed is:

1. A compound of the formula:

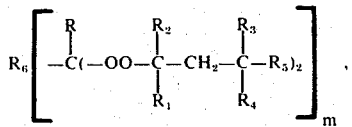

where: $R_1$, $R_2$, $R_3$ and $R_4$ are alkyl of 1–4 carbons and can be the same or different;

$R_5$ is alkyl of 1–8 carbons;

$m$ is 1 or 2; and

R and $R_6$ can be the same or different and are (when $m = 1$) substituted or unsubstituted alkyl or 1–10 carbons, alkenyl of 2–10 carbons, alkdienyl of 3–10 carbons, cycloalkyl of 3–10 carbons, cycloalkenyl of 3–10 carbons, aralkyl of 7–10 carbons or H, $R_6$ can also be aryl of 6–14 carbons when R is H, and R and $R_6$ can join to form a substituted or unsubstituted alkylene or alkenylene diradical of 3–11 carbons; the two Rs (when $m = 2$) can have the above definitions and can also join to form a substituted or unsubstituted alkylene diradical having 1–3 carbons in the alkylene chain; and $R_6$ is (when $m = 2$) a substituted or unsubstituted alkylene diradical having 1–8 carbons in the alkylene chain or, when both Rs and H, a substituted or unsubstituted phenylene diradical;

the substituents being selected from one or more of lower alkyl, carboxy, and lower alkoxycarbonyl.

2. Claim 1 where $R_1$, $R_2$, $R_3$ and $R_4$ are methyl.
3. Claim 2 where $R_5$ is methyl or $-CH_2C(CH_3)_2CH_3$.
4. Claim 2 where R and $R_5$ are methyl and m is 1.
5. Claim 4 where $R_6$ is methyl, ethyl, isopropyl, n-butyl, isobutyl, $-C_2H_4CH=C(CH_3)_2$,

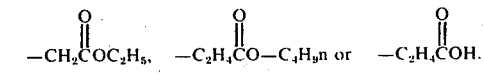

6. A compound according to claim 2 selected from 1,1-di-(t-octylperoxy) cyclohexane; 2-methyl-1,1-di-(t-octylperoxy) cyclohexane; 3-methyl-1,1-di-(t-octylperoxy) cyclohexane; 3,3-di-(t-octylperoxy) pentane; 3,3-di-(t-octylperoxy)-heptane; 4,4di-(t-octylperoxy) heptane; 2,2,4,4-tetra-(t-octylperoxy) pentane; 1,1-di-(t-octylperoxy)-1-phenylmethane; 3,7-dimethyl-1,1-di-(t-octylperoxy)-2,6-octadiene; 2,2-di-(t-octylperoxy) propane; and 3,3,5-trimethyl-1,1-di-(t-octylperoxy) cyclohexane.

7. 2,2-Di-(t-octylperoxy)propane.

* * * * *